United States Patent [19]

Whiteley

[11] Patent Number: 5,610,189

[45] Date of Patent: Mar. 11, 1997

[54] DISINFECTING COMPOSITION

[76] Inventor: Reginald K. Whiteley, 18 Glenside Street, Balgowlah Heights, NSW 2093, Australia

[21] Appl. No.: 295,741

[22] PCT Filed: Mar. 3, 1993

[86] PCT No.: PCT/AU93/00087

§ 371 Date: Nov. 7, 1994

§ 102(e) Date: Nov. 7, 1994

[87] PCT Pub. No.: WO93/17558

PCT Pub. Date: Sep. 16, 1993

[30] Foreign Application Priority Data

Mar. 3, 1992 [AU] Australia ............................. PL1145

[51] Int. Cl.$^6$ ........................ A01N 37/00; A01N 35/00; A01N 27/00
[52] U.S. Cl. ...................... 514/557; 514/557; 514/675; 514/693; 514/763; 514/937; 514/975
[58] Field of Search ...................... 514/557, 675, 514/693, 763, 937, 975

[56] References Cited

FOREIGN PATENT DOCUMENTS

| 7496881 | 3/1982 | Australia . |
| 1153267 | 9/1983 | Canada . |
| 0288689 | 3/1988 | European Pat. Off. . |
| WO8810122 | 12/1988 | WIPO . |
| WO9115190 | 10/1991 | WIPO . |

OTHER PUBLICATIONS

Sanyo Chem Ind Ltd., Sann 18, Oct. 1988, JO 3086–802–A, "Odorless Biocidal Emulsion For Agriculture –Comprises Terpene CPD. E. G. Limonene Terpinene, Emulsifier and Surface Active Agent E.G. Insecticide".

*Primary Examiner*—John W. Rollins
*Attorney, Agent, or Firm*—Poms, Smith, Lande & Rose

[57] ABSTRACT

A disinfecting composition comprising stable aqueous solutions of (a) a blend of biocidally active terpenes, (b) one or more biocidally active surfactants, (c) one or more proton donor type biocides, and (d) a salt of mono, di or trihydroxy aliphatic or aromatic acid wherein the blend of biocidally active terpenes is tea tree oil.

32 Claims, No Drawings

DISINFECTING COMPOSITION

BACKGROUND OF THE INVENTION

The present invention relates to disinfectant compositions, particularly disinfectant compositions for fabric.

The invention has been developed primarily for use as a disinfectant composition for heavily soiled and wet household fabrics and will be described hereinafter with reference to this application. However, it will be appreciated that the invention is not limited to this particular field of use.

The disinfection and deodorizing of heavily soiled and wet household fabrics is difficult for many reasons and is exacerbated by prolonged periods of wetness. Prolonged periods of wetness regularly occur due to such events as water leakage, broken water mains, storm damage and natural flooding disasters. Flooding due to natural disasters can represent a worst case scenario because carpets and fabrics are also soiled by mud and other debris which require extensive cleaning and disinfection to achieve restoration of fabric.

In the past, biocides have been employed to disinfect and deodorize wet household fabrics but most fibres employed in household fabric adsorb biocides. Accordingly, the fabric itself can inactivate many common biocidal molecules and render disinfection and deodorization ineffective over a large area of fabric. In an attempt to overcome this problem the concentration of active biocide has, in the past, been increased to overcome the loss of biocide by adsorption or a biocide, minimally reactive to fibres, is utilized to minimize the loss of biocide by adsorption.

However, many such fibres are also known to adsorb significant quantities of water, when wet, and the water adsorbed is known to alter the concentration of active biocides whether applied in high or low concentrations. The resultant dilution of biocide concentration levels significantly reduces biocide activity and the dilution effect can be even more significant when the biocides form part of a cleaning agent with surfactants, disinfectant and deodorants.

Ideally, an effective fabric disinfectant and deodorant should be capable of removing spots and stains encountered on most household fabrics and the effect of wet fabric can therefore reduce the efficiency of a cleaning agent formulated from the said disinfectants, deodorants and surfactants.

Another factor affecting the efficiency of biocides and cleaning agents incorporating biocides is that wetness of fabric, particularly in soft floor coverings, is often accompanied by the growth of microbes, mould and bacterial spores often already resident in the fabric before the fabric is wetted. The combination of wetness and organic soil provides an ideal nutrient medium for microbe growth such as algae, bacterial spores, moulds and microbes indigenous to natural water supplies and soil.

In addition, if the fabric is exposed to soiling and odours from household animal deposits such as urine or faeces under conditions of minimal domestic hygiene, disinfection and deodorization presents a major challenge because the deposits are associated with strongly odouriferrous and microbially active substances which remain in the fabric and contribute to the odour of the fabric.

The widely varying requirements imposed by the foregoing factors makes the formulation of an effective product which will both disinfect, deodorize and clean household fabrics successfully, exceedingly difficult. Indeed, at this time there is no single product available that overcomes the problems associated with the above factors, without side effects. This is despite the accumulated knowledge that is available on the formulation of disinfectants for other purposes.

The most difficult situations occur when fabrics are grossly fouled as occurs when houses are flooded as a result of pipe breakages and natural disasters.

Biocides are available that are able to kill, under laboratory conditions, a wide range of microbes that can be found in dry and wet household fabrics. Examples of such biocides are formaldehyde, glutaraldehyde and other dialdehydes, halogens such as bromine, chlorine and iodine, stronger oxidizing agents such as hydrogen peroxide and sodium peroxide, and low molecular weight alcohols such as ethanol and isopropanol. These biocides are generally accepted as "high level disinfectants" in hospitals. However, under practical conditions for household fabrics, all have serious practical limitations that restricts use by reason of either obnoxious odour (aldehydes), chemical toxicity and/or destructiveness (halogens), irritancy and toxicity (aldehydes), potential for fibre damage and/or dye reduction (oxidizing agents) or flammability (alcohols).

Likewise while many chemicals and chemical compositions are claimed to reduce, react with or otherwise eliminate offensive odours and disinfect fabrics (and indeed are regularly promoted for the deodorizing and/or perfuming of domestic carpeting) no existing product is effective in disinfecting, deodorizing and, if necessary, cleaning under the severe conditions imposed by prolonged periods of wetness.

It is an object of the invention, at least in its preferred embodiment, to ameliorate at least some of the deficiencies of the prior art.

SUMMARY OF THE INVENTION

In accordance with the present invention there is provided a disinfecting composition comprising (a) a blend of biocidally active terpenes, (b) one or more biocidally active surfactants, (c) one or more proton donor type biocides, and (d) a salt of a mono, di or trihydroxy aliphatic or aromatic acids wherein the blend of biocidally active terpenes is tea tree oil. Preferably, the blend is not less than 30% weight terpinen-4-ol and not greater than 15% weight 1,8-cineole.

Preferably, the surfactant is capable of solubilizing the terpene blend and the blend may be distilled or refined and/or naturally occurring or reconstituted. The biocides are preferably an aldehyde or ketone type.

In a preferred embodiment of the invention the salt is chosen from salts of the group consisting of citric acid, gluconic acid, glutaric acid, lactic acid, tartaric acid, dihydroxy tartaric acid, hydroxy propionic acid, hydroxy butyric acid, hydroxy cinnamic acid, hydroxy benzoic acid or gallic acid. Most preferably the salt is a sodium, potassium, ammonium or amine salt.

In a preferred embodiment there are at least two surfactants which are anionic, cationic, nonionic, amphoteric or zwitterion or a mixture of anionic and cationic.

In a further aspect of the present invention the composition also includes a deodorizing agent and that agent may be a perfume, or an odour absorbing or odour masking agent. Preferably, the composition also include a dye agent.

The one or more proton donor biocides, in a preferred embodiment, are selected from the group consisting of glyoxal, glutaraldehyde, succihdialdehyde, 6-acetoxy-2, 4-dimethyl-m-dioxane, 1,2-bis(hydroxymethyl)-5,5-dimethylhydantoin and hydroxymethyl-5,5-dimethylhydantoin, 5-chloro-2-methyl-4-isothiazolin-3-one and 2-methyl-4-isothiazolin-3-one.

The composition of the present invention is preferably for use in respect of fabric particularly carpet, upholstery and soft household furnishings.

It is most preferable that the composition of the invention have a pH of not less than 5.5 and not greater than 8.5 to minimize damage to surfaces and fabrics.

In a further aspect of the present invention, the quantity of terpene blend, surfactant and biocide may vary according to whether the composition in a ready-to-use or concentrate (to be diluted before use) format. If the product is in the concentrate format the terpene blend is 0.25 to 7.5% weight, the biocides are 0.25 to 7.5% weight and the surfactant is 0.25 to 10% weight. If the product is in a ready-to-use format the terpene blend is 0.01 to 0.5% weight, the biocides are 0.01 to 0.5% weight and the surfactant is 0.025 to 0.5% weight.

Preferably, the salt is in the amount of 0.5 to 7.5% in a concentrate format or 0.05 to 0.25% in ready-to-use format.

In yet a further aspect of the invention, the composition acts as a carrier for secondary compositions for the control of biological fouling. The secondary compositions may be miticides, insecticides, algaecides and fungicides.

DETAILED DESCRIPTION OF THE INVENTION

It has been discovered that effective and rapid disinfection and deodorizing of wet fabrics is achievable together with removal of common spots and stains. This is achieved by combining proportions of a biocide or several biocides with a biocidically active surfactant(s), biocidically active terpenes and a salt of an aliphatic or aromatic acid in a biocidical composition.

Where a solvent or other solubilizing agent is required to manufacture a stable composition the additional components are chosen for their ability to either compliment or assist in biocidal action without side effects such as residues on fibres that may either damage, discolour or cause soil pickup after use of the composition on fabric. It has been determined that the composition of the invention can be applied to fibres that have been treated with fluorocarbon soil repellent treatments and stain blocker resins of water repellent treatments without destruction or damage to the fibre treatments per se.

In a preferred embodiment, the composition of the present invention may also be appropriate for the control or management of household pests, mites and other biological fouling. In such a preferred embodiment, the composition of the present invention may serve as a vehicle or carrier for the transport of secondary compositions appropriate for the control of biological fouling from household pests, mites etc. It has been established in tests that the compositions may be carried on the composition of the present invention without interference with the biocidal activity of the composition of the present invention.

Examples of such secondary compositions are miticides such as benzyl alcohol and benzyl benzoate, insecticides such as natural and synthetic pyrethroids, algaecides and fungicides such as hydroxy benzoic acid esters, Dowcil (Dow Chemicals Inc., USA), Germall II (Sutton Laboratories Inc., USA), Fungaflor (Janssen Pharmaceutics, Belgium), phenoxyethanol, potassium sorbate and Myacids BT (The Boots Company PLC, UK) and Kathon WT (Rohm & Haas Inc., USA).

The composition of the present invention may comprise a stable aqueous solution of a biocidally active natural terpene blend based on the refined terpene rich oil of various species of the tea tree oil known as Oil of Melaleuca, terpinen-4-ol type. The preferred components of tea tree oils are defined in Australian Standard AS2782-1985 which states that acceptable commercial oils must contain not less than 30.0 percent weight of the major biocidally active ingredient terpinen-4-ol and not more than 15 percent weight 1,8-cineole content. The grade of tea tree oil used in the composition will preferably conform to this standard and such an oil may be as distilled or refined.

Reconstituted tea tree oils are available which are standardised as to composition and avoid variations in composition and odour frequently associated with naturally derived oils due to seasonal and regional factors. Provided the reconstituted oils conform to AS 2872-1985 such oils may be employed in the composition of the invention.

Tea tree oil is particularly effective as a disinfectant in both the vapour and liquid states particularly in situations where rapid lipid solubility is a factor in biocidal mechanisms. Tea tree oil is used for example as a vapour injected into air in air-conditioning systems where it has been demonstrated as effective against typical microbes found in air ducting. It has been shown to be particularly effective in eliminating bacteria and fungal spores from air ducting even under conditions of sustained high humidity in tropical areas.

The biocidally active terpenes employed in this invention, when properly formulated, penetrate into then evaporate slowly after applications to fabrics, allowing wet contact with microbes releasing biocidal vapour over a period of hours to sustain biocidal activity. Vapour provides a sustained biocidal atmosphere within the pile of fabrics which allows for slower penetration of biocidal substances, into soil masses containing microbes, into microbial spore coatings and soil masses within fouled fabrics. It also affords the opportunity for biocide to penetrate into the backing of underlay where used beneath carpeting.

Tea tree oil is also a very efficient solvent towards many organic soils found in household and commercial carpets. I have found a preferred concentration of tea tree oil of from 0.5 to 7.5 percent weight can be incorporated into a suitable concentrate product. This corresponds to a preferred minimum concentration of tea tree oil of from 0.010 to 0.75 percent weight which may be diluted according to the presentation of the fabric on which it is to be used. The more soiled the fabric, the greater the concentration of the composition and the less need for dilution.

The composition may also comprise a stable aqueous solution of one or more commercially available proton donor type biocides of either an aldehyde or ketone type to compliment the tea tree oil as a biocide.

The proton donor biocides, either aldehydes or ketones, I have found effective for use in conjunction with ea tree oil are of the group consisting of glyoxal, glutaraldehyde, succindialdehyde, Givguard DXN(6-acetoxy-2, 4-dimethyl-m-dioxane) Dantogard(1,2-bis(hydroxymethyl)-5,5-dimethylhydantoin and hydroxymethyl-5,5-dimethylhydantoin; Kathon WT, 5-chloro-2-methyl-4-isothiazolin-3-one and 2-methyl-4-isothiazolin-3-one. No doubt there are other like molecules which act as biocides by similar chemical mechanisms that could also be employed in similar manner by those skilled in the art.

Choice of proton donor will depend upon the biocidal spectrum required. Where emphasis is required on the disinfection of moulds and larger organisms particularly against slimes, moulds and algae including both water and soil borne organisms, a mixture of two aldehydes (of different classes and different biocidal spectrums) may be preferred as shown in Example 2 of Table 1.

The amount of aldehyde of ketone biocide required will vary with the condition of the fabric as presented for treatment but will generally be in the range of 0.25 to 3.5 percent weight as a concentrate or 0.01 to 0.5 percent weight if diluted for use. Because the biocides vary in volatility and in their biocidal spectrum, in particular against bacterial spore and larger organisms such as fungi, there can be advantage in employing a mixture of aldehydes. Such a mixtures are illustrated in Table 1 below.

Yet further, the composition may also comprise a stable aqueous solution of a biocidally active cationic or anionic surfactant or a compatible mixture thereof to both assist in solubilizing the terpene oil and to provide additional disinfecting power as well as cleaning ability for the removal of spots and stains.

It is also envisaged that the composition may also comprise a stable aqueous solution of a sodium, potassium, ammonium or amine salt of citric acid or other mono, di or trihydroxy aliphatic or aromatic acid chosen from the group consisting of citric acid, gluconic acid, glutaric acid, lactic acid, tartaric acid, dihydroxy tartaric acid, hydroxy propionic acid, hydroxy butyric acid, hydroxy cinnamic acid, hydroxy benzoic acid and gallic acid.

The use of a biocidally active surfactant, which may be either anionic or cationic can be used uniquely in conjunction with the sodium salt of citric acid or other hydroxy organic acids to solubilize the tea tree oil in the composition of the invention. The amount of neutralized hydroxy organic acid e.g. sodium citrate, appropriately varies from 0.25 to 7.5 percent of a concentrated product.

Most preferably, the anionic biocide is the sulfonic acid of either an aliphatic hydrocarbon containing from 8 to 18 carbon atoms, the sulfonic acid of a linear or branched chain alkyl benzene suitable for use in household detergents or the sulfonic acid of an alkyl or dialkyl naphthalene suitable for use as a commercial surfactant, either of which may be incorporated in the formulation in the range 0.50 to 15.0 percent weight of the total composition. The sodium or potassium salt of an alcohol sulphate containing from 8 to 14 carbon atoms is preferred on the grounds of optimal biocidal activity against the widest range of micro-organisms. Other anionic surfactants may also be available which can be adapted to perform a similar function to that described herein and known to those skilled in the art.

Preferably, a second surfactant is provided which will compliment the particular biocidal system and which may be either anionic, nonionic or amphoteric in nature to further assist in solubilizing the terpene oil without detracting from the biocidal activity of the finished product and/or to contribute to short or long term antimicrobial action after application of the product resulting therefrom.

A secondary surfactant is preferably used to assist in solubilizing larger quantities of tea tree oil in more concentrated products. The preferred surfactants are linear alcohol ethoxylates, linear alcohol or secondary alcohol sulphates, linear and secondary alkyl sulfonates and biocidally active amphoteric surfactants such as Tego 53 or 103. However, provided the chosen surfactant does not interfere with the biocidal performance of the end product almost any commercial surfactant could be employed for this purpose.

Where a quaternary surfactant is used, as in products with wider areas of application, a commercial biocidal surfactant suitable for formulating hospital quality disinfectants is preferably employed. Typically, an alkyl dimethyl benzyl ammonium chloride or a dual chain alkyl dimethyl benzyl ammonium chloride, bromide or iodide, or tetra alkyl phosphonium chloride (Belclene 350—Dow Chemicals Inc., USA) or like molecules are employed. In a preferred embodiment, 3(trimethoxysilyl) propylactadecyldimethyl ammonium chloride, (Biosil 5700—Dow Corning Corporation, USA) is well suited for use in these preparations. A commercial quaternary surfactant which is (Amended) compatible with anionic surfactants but which also exhibits useful biocidal activity can also be employed. The amount of quaternary surfactant as active matter should preferably range from 0.50 to 15.0 percent weight in a concentrate product or from 0.01 to 1.50 percent weight if required to be diluted.

More preferably a suitable perfume is added to make the odour of the finished product as attractive as practical to the average householder which is compatible with the chemical system involved. A dye may also be incorporated to give a distinctive colour to a product provided non-substantive to fibres under conditions of use.

As tea tree (melaleuca) oil has a characteristic odour it is advantageous to employ a perfume to make the overall product more cosmetically attractive to the consumer. The perfume may optionally contain a proprietary odour maskant or an acceptable perfume. The amount of perfume required will vary according to odour type but will generally be in the range 0.01 to 0.25 percent weight in a concentrated dilutable product.

Examples of compositions according to a preferred embodiment of the present invention are detailed in Table 1. These are manufactured by dissolving and mixing the various ingredients into demineralized water at room temperature in the order listed. It is most important that each ingredient be dissolved to yield a clear solution before the next ingredient is added into the solution. A portion of the water (up to 50 percent) can be withheld in the initial phase of manufacture and added when all ingredients are dissolved. The withholding of a portion of water applies more to stronger dilutable concentrates.

TABLE 1

TYPICAL COMPOSITIONS

| INGREDIENT | EXAMPLES | | | | |
|---|---|---|---|---|---|
| | 1 | 2 | 3 | 4 | 5 |
| | WEIGHT PERCENTAGE OF ACTIVES | | | | |
| BEL | — | 2.5 | — | — | — |
| BAC | — | — | — | 5.0 | — |
| 12A | — | 1.0 | — | 2.5 | — |
| DF3 | — | — | — | — | 3.0 |
| LAS | 0.2 | — | — | — | 1.5 |
| SLS | 0.1 | — | 3.5 | — | — |
| NaC | 0.5 | 2.5 | 2.5 | 5.5 | 3.5 |
| TTO | 0.13 | 3.0 | 2.5 | 3.5 | 3.5 |
| KWT | 0.05 | — | 0.8 | 1.5 | — |
| GXL | 0.05 | 1.0 | — | — | — |
| G11 | — | 2.0 | — | — | — |
| DXN | — | — | — | 1.5 | 1.5 |
| PER | 0.02 | 0.2 | 0.2 | 0.2 | 0.2 |
| H$_2$O | BAL | BAL | BAL | BAL | BAL |

Amounts of surfactants required in the above formulations may very slightly with different batches of natural tea tree oil.
LEGEND
BEL Belclene 350, Ciba Geigy Ltd.
BAC Benzalkonium chloride USP
12A Linear (C12) alcohol ethoxylate 12 mol ethlyene oxide
LAS Linear alkyl benzene sodium sulphonate
SLS Sodium dodecyl sulfate
DF3 Disodium n-decyl diphenylether disulphonate
NaC Sodium citrate anhydrous
TTO Tea Tree oil
GXL Glyoxal
G11 Germall 11, Sutton Laboratories Inc., USA
KWT Kathon WT, Rohm & Haas Inc.
DXN Givgard DXN, Ciba Geigy Ltd.
PER Perfume for cosmetic effect
H$_2$O Demineralized water
BAL Balance of the formulation to 100.0 percent weight.

With the exception of Example 1, which is intended to be a ready-to-use composition, the compositions can be diluted prior to use the extent of dilution varying according to the quantity of active ingredients in the particular formula and the degree of fouling on the particular household fabric. Dilutions of up to 100 to 1 can be made with the more concentrated products, e.g. Example 4, where the fouling on a particular fabric is minimal.

The pH of the compositions is critical with respect to optimizing the biocidal action of a particular formulation as it is in all household fabric treatments. It is especially important that the pH be optimized to avoid fibre damage in the case of woollen and some acrylic fibres. The pH of each of the concentrated solutions illustrated above may be adjusted with either sodium hydroxide or citric acid such that when diluted, as suggested the application pH will be in the range 5.5 to 8.5, with preference for a mildly acidic pH with anionic systems and a mildly alkaline pH for cationic systems in Table 1.

More specialised formulations can be prepared from the preceeding formulations to incorporate miticidal and insecticidal constituents. In these cases the main formulation can serve as a carrier for the miticide or insecticide or for a supplementary, semi-permanent biocide such as BIOSIL 5700. Examples of these modified formulations are as follows:

EXAMPLE 6

Added Residual Fungicide

The formula of Example 1 is modified by the addition of 0.25 percent weight of Fungaflor Grade R27 180. The pH of 100 gram of Example 1 is adjusted to pH 6.7 to 7.0 during manufacture. The Fungaflor Grade R27 180 is weighted accurately then slowly added into Example 1 with good agitation at ambient temperature. A clear to slightly translucent solution results. The product is then subjected to stability testing and other quality control procedures.

EXAMPLE 7

Added Residual Insecticide

Example 4 is modified by the addition of dispersible insecticidal concentrate by the following method.

PREMIX A. 1.0 gram of Tetramethrin is slowly added into a mixture of 5.0 gram of Consosolv C140 cycloparaffinic solvent (Dupont Inc., USA) and 5.0 grams of benzyl alcohol while being stirred. To this is added 1.0 gram of Teric 9A6 (ICI Australia Ltd.), 1 gram of Teric 12A12 (ICI Australia Ltd.) and 2.0 gram of Gardiquat 1450 (Albright & Wilson Australia Ltd.). The mixture is stirred at room temperature until a clear solution results.

PREMIX B. 100.0 gram of Example 4 is slowly diluted with 100.0 gram of demineralized water while stirring. To this solution is very slowly added 4.0 gram of PREMIX A with very efficient stirring. Stirring is continued for a minimum of 30 minutes until a stable product results. Variations of this method of manufacture will be readily discernable to suit local conditions including surfactant sources by those skilled in the art. The product is then checked for stability and such other quality control characteristics.

EXAMPLE 8

Added Miticide

Example 3 is modified by the addition of a readily dispersible solution of miticides, benzyl alcohol and benzyl benzoate.

PREMIX C. 5.0 grams of benzyl benzoate is mixed with 5.0 gram of benzyl alcohol and 5.0 gram of benzyl dipropylene glycol. This is dissolved, if need be by gentle warming. 12.0 gram of Dowcide 3B2 is added and dissolved in the solution.

PREMIX D. 100.0 gram of Example 3 is diluted with 100.0 gram of demineralized water while stirring. 15.0 gram of PREMIX C is very slowly added into the solution under strong agitation and the resulting solution mixed for a minimum of 30 minutes at room temperature. The solution is checked for stability and such other quality control characteristics as required.

Variations of the latter method of incorporating benzyl benzoate and benzyl alcohol into surfactant solutions will be readily discerned by those skilled in the art, as will be adjustments to production in the advent that minor instability of particular batches of product is noted.

Because of the wide range of conditions that are found in well-worn fouled, carpeting it is not yet possible to design realistic in-situ type laboratory tests to evaluate the effect of the compositions on all manner of situations. Actual field tests are required under practical conditions where it is known that existing products are inadequate or ineffective. These are carried out on soiled carpeting freshly removed from private houses or commercial buildings that are heavily soiled and exhibit strong smelling odours.

Such a carpet is cut into a number of 1 meter squares according to the number of samples to be tested. These are then uniformly lightly moistened and sealed in plastic bags for 7 days at room temperature to amplify odour producing processes. At the end of this period each piece is cleaned with a high quality carpet injection compound conforming to Australian Standard AS 3733-1990, e.g. Swiftclean (Whiteley Chemicals Australia Pty. Ltd.) using the method recommended in International Draft Standard, Injection Cleaning Method, ISO/7C38/SC12/WG8 dated Jun. 28, 1991. The cleaned squares are then sprayed with disinfectant/deodorant in accordance with manufacturers instructions and hung to dry. Appearance and odour are then noted at regular intervals during and after drying by a trained observer.

Three types of carpet were evaluated in a series of tests both in the USA (by SCS associates, Cochranville, Pa., USA) and Australia. In Series A the carpeting was headily fouled with animal debris including cat debris and general soils. In Series B water damaged, heavily soiled industrial carpeting was employed. In Series C flood damaged carpeting was used.

Testing in the USA was conducted on medium weight nylon carpet of both loop pile and cut pile construction. Three leading retail carpet disinfectant/deodorants were compared with Example 3. In Australia tests were conducted on medium weight wool and wool-nylon blend carpeting. Three industrial carpet disinfectant-deodorants were compared with Example 3. Tests were also carried out using Example 3 in both countries to establish safety of this formulation against 5th generation fluorocarbon treated carpet.

In all test series Example 3 gave the quickest rate of reduction of odour.

In both the USA and in Australia tests, Example 3 was the only formula that totally deodorised both animal soiled and flood soiled carpeting with a single injection cleaning operation followed by a single spray of disinfectant/deodorant.

Example 3 also proved non-damaging to 5-th generation fluorocarbon treatments on both wool and nylon carpeting.

I claim:

1. A disinfecting composition comprising stable aqueous solutions of:
   (a) a blend of biocidally active terpenes;
   (b) one or more biocidally active surfactants;
   (c) one or more proton donor type biocides; and
   (d) a salt of mono, di or trihydroxy aliphatic or aromatic acid;
   wherein the blend of biocidally active terpenes is tea tree oil.

2. A composition in accordance with claim 1 wherein the tea tree oil is not less than 30% weight terpinen-4-ol and not greater than 15% weight 1,8 cineole.

3. A composition according to claim 2 wherein the blend is distilled or refined.

4. A composition according to claim 1 wherein the blend of biocidally active terpenes is a naturally occurring oil.

5. A composition according to claim 1 wherein the biocides are aldehyde or ketone type.

6. A composition according to claim 5 wherein the one or more proton donor biocides are selected from the group consisting of: glyoxal; glutaraldehyde; succidialdehyde; 6-acetoxy-2; 4-dimethyl-m-dioxane; 1,2-bis (hydroxymethyl)-5,5-dimethylhydantoin and hydroxymethyl-5,5-dimethylhydantoin; and 5-chloro-2-methyl-4-isothiazolin-3-one and 2-methyl-4-isothiazolin-3-one.

7. A composition according to claim 1 wherein the surfactant is capable of solubilizing the terpene blend.

8. A composition according to claim 1 wherein the salt is chosen from salts of the group consisting of citric acid, gluconic acid, glutaric acid, lactic acid, tartaric acid, dihydroxy tartaric acid, hydroxy propionic acid, hydroxy butyric acid, hydroxy cinnamic acid, hydroxy benzoic acid or gallic acid.

9. A composition according to claim 8 wherein the salt is a sodium, potassium, ammonium or amine salt.

10. A composition according to claim 9 wherein the one or both of the surfactants are anionic, cationic, nonionic, amphotenic or zwitterion or a mixture of cationic and nonionic.

11. A composition according to claim 8 wherein the concentration of said salt in said solution is 0.5 to 7.5% weight.

12. A composition according to claim 8 wherein the concentration of said salt in said solution is 0.05 to 0.25% weight.

13. A composition according to claim 1 wherein the composition includes at least two surfactants.

14. A composition according to claim 1 wherein the composition also includes a deodorizing agent.

15. A composition according to claim 14 wherein the deodorizing agent is a perfume, odor absorbing or odor masking agent.

16. A composition in accordance with claim 15 wherein the perfume is present in the amount of 0.01 to 0.25% weight.

17. A composition according to claim 1 wherein the composition also includes a dye agent.

18. A composition according to claim 1 wherein the pH of the composition is not less than 5.5 and not greater than 8.5.

19. A composition according to claim 1 wherein the concentration of said terpene blend in said solution is 0.25 to 7.5% weight.

20. A composition according to claim 1 wherein the concentration of said terpene blend in said solution is 0.01 to 0.5% weight.

21. A composition according to claim 1 wherein the concentration of biocides in said solution is 0.25 to 7.5% weight.

22. A composition according to claim 1 wherein the concentration of said biocides in said solution is 0.01 to 0.5% weight.

23. A composition according to claim 1 wherein the concentration of said surfactant in said solution is 0.25 to 10% weight.

24. A composition according to claim 1 wherein the surfactant in said solution is 0.025 to 0.5% weight.

25. A composition according to claim 1 wherein the composition further comprises a compound for the control of biological fouling, said compound being selected from the group consisting of miticides, insecticides algaecides and fungicides.

26. A composition in accordance with claim 25 wherein the miticides are benzyl alcohol or benzl benzoate, the insecticides are natural and synthetic pyrethroids, and the algaecides and fungicides are hydroxy benzoic acid esters, Dowcil, Germall II, Fungaflor, phenoxyethanol, potassium, sorbate, Myacide BT or Kathon WT.

27. A composition according to claim 1 wherein said surfactant is a sodium or potassium salt and wherein said sodium or potassium salt is a salt of an alcohol sulphate containing from 8 to 14 carbon atoms.

28. A composition according to claim 1 wherein the surfactant is a quaternary surfactant.

29. A composition in accordance with claim 28 wherein the surfactant is present in the amount of 0.50 to 15% weight.

30. A composition according to claim 1 wherein the blend of biocidally active terpenes is a reconstituted oil.

31. A method of treating fabric comprising the steps of:
    preparing the fabric by cleaning the fabric with a surfactant, and
    applying disinfectant composition in accordance with the composition as claimed in claim 1.

32. A composition according to claim 31 wherein the fabric is carpet, upholstery or soft household furnishings.

* * * * *